US007365176B2

(12) United States Patent
Smith et al.

(10) Patent No.: US 7,365,176 B2
(45) Date of Patent: Apr. 29, 2008

(54) DETECTION OF EPSTEIN-BARR VIRUS

(75) Inventors: Thomas F. Smith, Rochester, MN (US); Mark J. Espy, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/255,217

(22) Filed: Sep. 26, 2002

(65) Prior Publication Data

US 2004/0063091 A1  Apr. 1, 2004

(51) Int. Cl.
*C07H 21/02* (2006.01)
*C07H 21/04* (2006.01)
*C12Q 1/68* (2006.01)

(52) U.S. Cl. ............... 536/23.1; 536/23.32; 536/24.33; 435/6

(58) Field of Classification Search ............... 536/22.1, 536/23.1, 24.33, 24.31, 24.32; 435/6, 91.2
See application file for complete search history.

(56) References Cited

U.S. PATENT DOCUMENTS

| 5,702,895 | A | | 12/1997 | Matsunaga et al. ............ 635/6 |
|---|---|---|---|---|
| 5,744,301 | A | * | 4/1998 | Birkenbach et al. ........... 435/6 |
| 5,837,452 | A | | 11/1998 | Clark et al. ..................... 435/6 |
| 6,593,093 | B1 | | 7/2003 | Uhl et al. ...................... 635/6 |
| 6,790,952 | B2 | * | 9/2004 | Groen et al. ............. 536/24.33 |
| 7,160,997 | B2 | * | 1/2007 | Chou et al. ................ 536/24.3 |
| 2002/0182634 | A1 | * | 12/2002 | Espy et al. ................... 435/7.1 |

FOREIGN PATENT DOCUMENTS

| EP | 269 764 | 6/1988 |
|---|---|---|
| EP | 0 338 591 | 10/1989 |
| EP | 0 526 876 | 2/1993 |
| EP | 1 045 033 | 10/2000 |
| EP | 1 160 333 | 12/2001 |
| WO | WO 98/48046 | 10/1998 |
| WO | WO 99/19466 | 4/1999 |
| WO | WO 99/45155 * | 9/1999 |
| WO | WO 9945155 A2 * | 9/1999 |
| WO | WO 00/37646 | 6/2000 |
| WO | WO 00/70096 | 11/2000 |
| WO | WO 01/12803 | 2/2001 |
| WO | WO 01/23604 | 4/2001 |
| WO | WO 02/18660 | 3/2002 |
| WO | WO 02/34771 | 5/2002 |
| WO | WO 02/61390 | 8/2002 |
| WO | WO 02/092818 | 11/2002 |
| WO | WO 03/025216 | 3/2003 |
| WO | WO 03/068918 | 8/2003 |
| WO | WO 03/093306 | 11/2003 |

OTHER PUBLICATIONS

Busson et al. Sequence polymorphism in the Epstein-Barr virus latent membrane protein (LMP)-2 gene. J Gen. Virology, vol. 76, pp. 139-145, 1995.*
Buck et al. Design startegies and performance of custom DNA sequencing primers. Biotechniques, vol. 27, No. 3, pp. 528-536, 1999.*
Lowe et al. A computer program for selection of oligonucleotide primers for polymerase chain reactions. Nucleic Acids Research, vol. 18, No. 7, pp. 1757-1761, 1990.*
Brink et al., "Nucleic Acid Sequence-Based Amplification, A New Method for Analysis of Spliced and Unspliced Epstein-Barr Virus Latent Transcripts, and Its Comparison with Reverse Transcriptase PCR," *J. Clin. Microbiol.*, 1998, 36(11):3164-3169.
Caplin et al., "LightCycler™ hybridization probes; The most direct way to monitor PCR amplification for quantification and mutation detection," *Biochemica*, 1999, 1:5-8.
Espy et al., "Quantification of Epstein-Barr Virus (EBV) Viral Load in Transplant Patients by LightCycler PCR," *Abstracts of the General Meeting of the American Society for Microbiology*, 101st General Meeting, May 20-24, 2001, 101:182, Abstract No. C-148.
Espy et al., "Diagnosis of Varicella-Zoster Virus Infections in the Clinical Laboratory by LightCycler PCT," *J. Clin. Microbiol.*, 2000, 38(9):3187-3189.
Espy et al., "Diagnosis of Herpes Simplex Virus Infections in the Clinical Laboratory by LightCycler PCR," *J. Clin. Microbiol.*, 2000, 38(2):795-799.
Espy et al., "Detection of Smallpox Virus DNA by LightCycler PCR," *J. Clin. Microbiol.*, 2002, 40(6):1985-1988.
Sample et al., "Two Related Epstein-Barr Virus Membrane Proteins are Encoded by Separate Genes," *J. Virol.*, 1989, 63(2):933-937.
Smith, "Application of Lightcycler Real Time PCR in Clinical Virology," *Clin. Chem. Lab. Med.*, 2001, Special Supplement, 39:S60, Abstract No. ISW14-2.
Telenti et al., "Detection of Epstein-Barr Virus by Polymerase Chain Reaction," *J. Clin. Microbiol.*, 1990, 28(10):2187-2190.
Abd-Elsalam et al., "Bioinformatic tools and guideline for PCR primer design," *African Journal of Biotechnology*, 2003, 2:91-95.
Ballard et al., "Comparison of Three PCR Primer Sets for Identification of vanB Gene Carriage in Feces and Correlation with Carriage of Vancomycin-Resistant Enterococci: Interference by vanB-Containing *Anaerobic bacilli*," *Antimicrobial Agents and Chemotherapy*, 2005, vol. 49, No. 1, pp. 77-81.
Csordas et al., "Comparison of primers for the detection of *Salmonella enterica* using real-time PCR," *Letter in Applied Microbiology*, 2004, 39:187-193.
Elnifro et al., "Multiplex PCR: Optimization and Application in Diagnostic Virology," *Clinical Microbiology Reviews*, 2000, vol. 13, No. 4, pp. 559-570.
Tichopad et al., "Inhibition of real-time RT-PCR quantification due to tissue-specific contaminants," *Molecular and Cellular Probes*, 2004, 18:45-50.

(Continued)

Primary Examiner—Suryaprabha Chunduru
(74) Attorney, Agent, or Firm—Fish & Richardson P.C.

(57) ABSTRACT

The invention provides methods to detect EBV in biological samples using real-time PCR. Primers and probes for the detection of EBV are provided by the invention. Articles of manufacture containing such primers and probes for detecting EBV are further provided by the invention.

3 Claims, No Drawings

OTHER PUBLICATIONS

Bergeron et al., "Rapid Detection of Group B Streptococci in Pregnant Women at Delivery," *New England J. Med.*, 2000, 343(3):175-179.

Ke et al., "Development of conventional and real-time PCR assays for the rapid detection of group B streptococci," *Clin. Chem.*, 2000, 46(3):324-331.

Ryncarz et al., "Development of a High-Throughput Quantitative Assay for Detecting Herpes Simplex Virus DNA in Clinical Samples," *J. Clin. Microbiol.*, 1999, 37:1941-1947.

Holland et al., "PCR Detection of *Escherichia coli* O157:H7 Directly from Stools: Evaluation of Commercial Extraction Methods for Purifying Fecal DNA," *J. Clin. Microbiol.*, 2000, 38:4108-4113.

Machiels et al., "New Protocol for DNA Extraction of Stool," *BioTechniques*, 2000, 28:286-290.

McOrist et al., "A comparison of five methods for extraction of bacterial DNA from human faecal samples," *J. Microbiol. Meth.*, 2002, 50:131-139.

Van Der Hoek et al., "Isolation of Human Immunodeficiency Virus Type 1 (HIV-1) RNA from Feces by a Simple Method and Difference between HIV-1 Subpopulations in Feces and Serum," *J. Clin. Microbiol.*, 1995, 33:581-588.

Arthur et al., "Enterococcus faecium transposon Tn1546 transposase, resolvase, vanR, vanS, vanH, vanA, vanX, vanY and teicoplanin resistance protein (vanZ) genes, complete cds," 1993, database accession No. M97297.

Grisold et al., "Detection of Methicillin-Resistant *Staphylococcus aureus* and Simultaneous Confirmation by Automated Nucleic Acid Extraction and Real-Time PCR," *J. Clin. Microbiol.*, 2002, 40:2392-2397.

Huletsky et al., "Rapid Detection of Vancomycin-Resistant Enterococci Directly from Rectal Swabs by Real-Time PCR Using the Smart Cycler," *Abstracts of the Interscience Conference on Antimicrobial Agents and Chemotherapy*, Chicago, Illinois, Sep. 22-25, 2001, 41:409 (Abstract K-1195).

Ito et al., "*Staphylococcus aureus* DNA, type-I staphylococcal cassette chromosome mec," 1999, database accession No. AB033763.

"LightCycler-FastStart DNA Master Hybridization Probes," 1000 Roche Diagnostics GmbH Technical Manual, retrieved from the internet on Feb. 6, 2004: http://www.roche-applied-science.com.

Palladino et al., "Real-time PCR for the rapid detection of *vanA* and *vanB* genes," *Diagnostic Microbiology and Infectious Disease*, 2003, 45:81-84.

Palladino et al., "Rapid Detection of *vanA* and *vanB* Genes Directly from Clinical Specimens and Enrichment Broths by Real-Time Multiplex PCR Assay," *J. Clin. Microbiol.*, 2003, 41:2483-2486.

Patel et al., "*Enterococcus faecalis* vancomycin resistance protein vanB gene, partial cds," 1997, database accession No. U72704.

Patel et al., "*Enterococcus faecium* vancomycin resistance protein B (vanB) gene, partial cds," 1997, database accession No. U94528.

Petrich et al., "Direct detection of *vanA* and *vanB* genes in clinical specimens for rapid identification of vancomycin resistant enterococci (VRE) using multiplex PCR," *Molecular and Cellular Probes*, 1999, 13:275-281.

Reischl et al., "Rapid Identification of Methicillin-Resistant *Staphylococcus aureus* and Simultaneous Species Confirmation Using Real-Time Fluorescence PCR," *J. Clin. Microbiol.*, 2000, 38:2429-2433.

Sloan et al., "Evaluation of a Combined LightCycler Assay for the Detection of vanA, vanB, and vanB-2/3 Genes in Enterococci," *Abstracts of the General Meeting of the American Society for Microbiology*, 2002, 102:143 (Abstract C-242).

Al-Robaiy et al., "Rapid Competitive PCR Using Melting Curve Analysis for DNA Quantification," *BioTechniques*, 2001, 31:1382-1388.

Bélanger et al., "Rapid Detection of Shiga Toxin-Producing Bacteria in Feces by Multiplex PCR with Molecular Beacons on the Smart Cycler," *J. Clin. Microbiol.*, 2002, 40:1436-1440.

Bellin et al., "Rapid Detection of Enterohemorrhagic *Escherichia coli* by Real-Time PCR with Fluorescent Hybridization Probes," *J. Clin. Microbiol.*, 2001, 39:370-374.

Chen et al., An Automated Fluorescent PCR Method for Detection of Shiga Toxin-Producing *Escherichia coli* in Foods,: *Appl. Environ. Microbiol.*, 1998, 64:4210-4216.

Didenko, "DNA Probes Using Fluorescence Resonance Energy Transfer (FRET): Designs and Applications," *BioTechniques*, 2001, 31:1106-1121.

Ramotar et al., "Direct Detection of Verotoxin-Producing *Escherichia coli* in Stool Samples by PCR," *J. Clin. Microbiol.*, 1995, 33:519-524.

Livak et al., "Oligonucleotides with Fluorescent Dyes at Opposite Ends Provide A Quenched Probe System Useful for Detecting PCR Product and Nucleic Acid Hybridization," *Genome Research*, 1995, 4:357-362.

Bassler et al., "Use of a Fluorogenic Probe in a PCR-Based Assay for the Detection of *Listeria monocytogenes*," *Applied and Environmental Microbiology*, 1995, 61(10):3724-3728.

* cited by examiner

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide

<400> SEQUENCE: 1
atgaggaacg tgaatctaat ga                                              22

<210> SEQ ID NO 2
<211> LENGTH: 23
<212> TYPE: DNA
<213> ORGANISM: Artificial Sequence
<220> FEATURE:
<223> OTHER INFORMATION: Oligonucleotide

<400> SEQUENCE: 2
tacagataga tggcactctt acc                                             23

<210> SEQ ID NO 3
<211> LENGTH: 32
<212> TYPE: DNA
<213> ORGANISM: Artificial Sequence
<220> FEATURE:
<223> OTHER INFORMATION: Oligonucleotide

<400> SEQUENCE: 3
ctactctcca cgggatgact catctcaaca ca                                   32

<210> SEQ ID NO 4
<211> LENGTH: 17
<212> TYPE: DNA
<213> ORGANISM: Artificial Sequence
<220> FEATURE:
<223> OTHER INFORMATION: Oligonucleotide

<400> SEQUENCE: 4
gaagaagcgg gcagagg                                                    17
```

DETECTION OF EPSTEIN-BARR VIRUS

TECHNICAL FIELD

This invention relates to viral diagnostics, and more particularly to detection of Epstein-Barr virus (EBV).

BACKGROUND

Epstein-Barr virus (EBV) is a member of the family Herpesviridae. EBV nucleic acid is double-stranded and consists of 172 Kb. EBV DNA is in a linear form in mature infectious virus particles and is in a circular episomal form in cells latently infected with the virus. EBV is the major cause of infectious mononucleosis, an acute, generally benign lymphoproliferative disease. Infection with EBV usually occurs by 10 years of age; 70 to 90% of children have been infected with EBV. Usually, infection in children is asymptomatic or mild and may be associated with minor illnesses such as upper respiratory tract infection, pharyngitis, tonsillitis, bronchitis, and otitis media. Other persistent EBV infections, such as those accruing in patients during the post-transplantation period, are common.

EBV has become a recognized cause of central nervous system infection and lymphoproliferative disorders (PTLD), and AIDS-related lymphomas. PTLD consists of a heterogenous group of B-cell neoplasias that arise in a setting of immunosuppression and are associated with EBV infection especially in patients lacking antibodies to this virus. The incidence of PTLD ranges from 1% for renal transplant recipients, but can be as high as 9% for heart/lung and 12% for pancreas transplant patients. EBV DNA can be detected in blood lymphocytes from patients with EBV infection, and quantitative evaluation of EBV DNA has been shown to correlate highly with the subsequent (3-4 month) development of PTLD in susceptible patients.

SUMMARY

The invention provides for methods of identifying Epstein-Barr virus (EBV) in a biological sample. Primers and probes for detecting EBV are provided by the invention, as are kits containing such primers and probes. Methods of the invention can be used to rapidly identify EBV DNA from specimens for diagnosis of EBV infection. Using specific primers and probes, the methods of the invention include amplifying and monitoring the development of specific amplification products using fluorescence resonance energy transfer (FRET).

In one aspect of the invention, there is provided a method for detecting the presence or absence of EBV in a biological sample from an individual. The method to detect EBV includes performing at least one cycling step, which includes an amplifying step and a hybridizing step. The amplifying step includes contacting the sample with a pair of latent membrane protein (lmp) primers to produce a lmp amplification product if an EBV lmp nucleic acid molecule is present in the sample. The hybridizing step includes contacting the sample with a pair of lmp probes. Generally, the members of the pair of lmp probes hybridize within no more than five nucleotides of each other. A first lmp probe of the pair of lmp probes is typically labeled with a donor fluorescent moiety and a second lmp probe of the pair of lmp probes is labeled with a corresponding acceptor fluorescent moiety. The method further includes detecting the presence or absence of FRET between the donor fluorescent moiety of the first lmp probe and the acceptor fluorescent moiety of the second lmp probe. The presence of FRET is usually indicative of the presence of EBV in the sample, while the absence of FRET is usually indicative of the absence of EBV in the sample.

A pair of lmp primers generally includes a first lmp primer and a second lmp primer. A first lmp primer can include the sequence 5'-ATG AGG AAC GTG AAT CTA ATG A-3' (SEQ ID NO:1), and a second lmp primer can include the sequence 5'-TAC AGA TAG ATG GCA CTC TTA CC-3' (SEQ ID NO:2). A first lmp probe can include the sequence 5'-CTA CTC TCC ACG GGA TGA CTC ATC TCA ACA CA-3' (SEQ ID NO:3), and a second lmp probe can include the sequence 5'-GAA GAA GCG GGC AGA GG-3' (SEQ ID NO:4).

In some aspects, one of the lmp primers can be labeled with a fluorescent moiety (either a donor or acceptor, as appropriate) and can take the place of one of the lmp probes.

The members of the pair of lmp probes can hybridize within no more than two nucleotides of each other, or can hybridize within no more than one nucleotide of each other. A representative donor fluorescent moiety is fluorescein, and corresponding acceptor fluorescent moieties include LC-Red 640, LC-Red 705, Cy5, and Cy5.5. Additional corresponding donor and acceptor fluorescent moieties are known in the art.

In one aspect, the detecting step includes exciting the sample at a wavelength absorbed by the donor fluorescent moiety and visualizing and/or measuring the wavelength emitted by the acceptor fluorescent moiety (i.e., visualizing and/or measuring FRET). In another aspect, the detecting step includes quantitating the FRET. In yet another aspect, the detecting step can be performed after each cycling step (e.g., in real-time).

Generally, the presence of FRET within 45 cycles (e.g., 20, 25, 30, 35, or 40 cycles) indicates the presence of an EBV infection in the individual. In addition, determining the melting temperature between one or both of the lmp probe(s) and the lmp amplification product can confirm the presence or absence of the EBV.

Representative biological sample include dermal swabs, lymphoid tissue, cerebrospinal fluid, blood, sputum, bronchio-alveolar lavage, bronchial aspirates, lung tissue, and urine. The above-described methods can further include preventing amplification of a contaminant nucleic acid. Preventing amplification can include performing the amplifying step in the presence of uracil and treating the sample with uracil-DNA glycosylase prior to amplifying.

In addition, the cycling step can be performed on a control sample. A control sample can include the same portion of the EBV lmp nucleic acid molecule. Alternatively, a control sample can include a nucleic acid molecule other than an EBV lmp nucleic acid molecule. Cycling steps can be performed on such a control sample using a pair of control primers and a pair of control probes. The control primers and probes are other than lmp primers and probes. One or more amplifying steps produces a control amplification product. Each of the control probes hybridizes to the control amplification product.

In another aspect of the invention, there are provided articles of manufacture, or kits. Kits of the invention can include a pair of lmp primers, and a pair of lmp probes, and a donor and corresponding acceptor fluorescent moieties. For example, the first lmp primer provided in a kit of the invention can have the sequence 5'-ATG AGG AAC GTG AAT CTA ATG A-3' (SEQ ID NO:1) and the second lmp primer can have the sequence 5'-TAC AGA TAG ATG GCA CTC TTA CC-3' (SEQ ID NO:2). The first lmp probe provided in a kit of the invention can have the sequence 5'-CTA CTC TCC ACG GGA TGA CTC ATC TCA ACA CA-3' (SEQ ID NO:3) and the second lmp probe can have the sequence 5'-GAA GAA GCG GGC AGA GG-3' (SEQ ID NO:4).

Articles of manufacture can include fluorophoric moieties for labeling the probes or the probes can be already labeled with donor and corresponding acceptor fluorescent moieties. The article of manufacture can also include a package insert having instructions thereon for using the primers, probes, and fluorophoric moieties to detect the presence or absence of EBV in a sample.

In yet another aspect of the invention, there is provided a method for detecting the presence or absence of EBV in a biological sample from an individual. Such a method includes performing at least one cycling step. A cycling step can include an amplifying step and a hybridizing step. Generally, an amplifying step includes contacting the sample with a pair of lmp primers to produce a lmp amplification product if an EBV lmp nucleic acid molecule is present in the sample. Generally, a hybridizing step includes contacting the sample with a lmp probe. Such a lmp probe is usually labeled with a donor fluorescent moiety and a corresponding acceptor fluorescent moiety. The method further includes detecting the presence or absence of fluorescence resonance energy transfer (FRET) between the donor fluorescent moiety and the acceptor fluorescent moiety of the lmp probe. The presence or absence of fluorescence is indicative of the presence or absence of EBV in said sample.

In one aspect, amplification can employ a polymerase enzyme having 5' to 3' exonuclease activity. Thus, the first and second fluorescent moieties would be within no more than 5 nucleotides of each other along the length of the probe. In another aspect, the lmp probe includes a nucleic acid sequence that permits secondary structure formation. Such secondary structure formation generally results in spatial proximity between the first and second fluorescent moiety. According to this method, the second fluorescent moiety on a probe can be a quencher.

In another aspect of the invention, there is provided a method for detecting the presence or absence of EBV in a biological sample from an individual. Such a method includes performing at least one cycling step. A cycling step can include an amplifying step and a dye-binding step. An amplifying step generally includes contacting the sample with a pair of lmp primers to produce a lmp amplification product if an EBV lmp nucleic acid molecule is present in the sample. A dye-binding step generally includes contacting the lmp amplification product with a double-stranded DNA binding dye. The method further includes detecting the presence or absence of binding of the double-stranded DNA binding dye into the amplification product. According to the invention, the presence of binding is typically indicative of the presence of EBV in the sample, and the absence of binding is typically indicative of the absence of EBV in the sample. Such a method can further include the steps of determining the melting temperature between the lmp amplification product and the double-stranded DNA binding dye. Generally, the melting temperature confirms the presence or absence of EBV. Representative double-stranded DNA binding dyes include SYBRGreenI®, SYBRGold®, and ethidium bromide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

A real-time assay for qualitatively and quantitatively detecting EBV in a biological sample that is more sensitive and specific than existing assays is described herein. The assay detects EBV in cerebrospinal fluid (CSF) of patients with central nervous system (CNS) disease. The assay also detects EBV in blood or plasma specimens from patients with viremia. The invention provides primers and probes for detecting EBV infections and articles of manufacture containing such primers and probes. The increased sensitivity of real-time PCR for detection of EBV compared to other methods, as well as the improved features of real-time PCR including sample containment and real-time detection of the amplified product, make feasible the implementation of this technology for routine diagnosis of EBV infections in the clinical laboratory.

EBV Nucleic Acids and Oligonucleotides

The invention provides methods to detect EBV by amplifying, for example, a portion of the EBV latent membrane protein (lmp) nucleic acid. EBV nucleic acids other than those exemplified herein (e.g., other than lmp) also can be used to detect EBV in a sample and are known to those of skill in the art. The nucleic acid sequence of EBV lmp is available (see, for example, GenBank Accession No. X81759). Specifically, primers and probes to amplify and detect EBV lmp nucleic acid molecules are provided by the invention.

Primers that amplify an EBV nucleic acid molecule, e.g., EBV lmp, can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 30 nucleotides in length. As used herein, "lmp primers" refers to oligonucleotide primers that anneal specifically to lmp nucleic acid sequences and initiate synthesis therefrom under appropriate conditions.

Designing oligonucleotides to be used as hybridization probes can be performed in a manner similar to the design of primers, although the members of a pair of probes preferably anneal to an amplification product within no more than 5 nucleotides of each other on the same strand such that FRET can occur (e.g., within no more than 1, 2, 3, or 4 nucleotides of each other). This minimal degree of separation typically brings the respective fluorescent moieties into sufficient proximity such that FRET occurs. It is to be understood, however, that other separation distances (e.g., 6 or more nucleotides) are possible provided the fluorescent moieties are appropriately positioned relative to each other (for example, with a linker arm) such that FRET can occur. In addition, probes can be designed to hybridize to targets that contain a polymorphism or mutation, thereby allowing differential detection of EBV strains or mutants based on either absolute hybridization of different pairs of probes corresponding to the particular EBV strain or mutant to be distinguished or differential melting temperatures between, for example, members of a pair of probes and each amplification product corresponding to a EBV strain or mutant to be distinguished. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 30 nucleotides in length. As used herein, "lmp probes" refers to oligonucleotide probes that specifically anneal to lmp amplification products.

Constructs of the invention include vectors containing an EBV nucleic acid molecule, e.g., EBV lmp or a fragment thereof. Constructs of the invention can be used, for example, as control template nucleic acid molecules. Vectors suitable for use in the present invention are commercially available and/or produced by recombinant DNA technology methods routine in the art. EBV lmp nucleic acid molecules can be obtained, for example, by chemical synthesis, direct cloning from EBV, or by PCR amplification. An EBV nucleic acid molecule or fragment thereof can be operably linked to a promoter or other regulatory element such as an enhancer sequence, a response element, or an inducible element that modulates expression of the EBV nucleic acid molecule. As used herein, operably linking refers to connecting a promoter and/or other regulatory elements to an EBV nucleic acid molecule in such a way as to permit and/or regulate expression of the EBV nucleic acid molecule. A promoter that does not normally direct expression of EBV lmp can be used to direct transcription of a lmp nucleic acid using, for example, a viral polymerase, a bacterial polymerase, or a eukaryotic RNA polymerase II. Alternatively, the lmp native promoter can be used to direct transcription of a lmp nucleic acid, respectively, using, for example, an RNA polymerase enzyme (e.g., RNA polymerase II). In addition, operably linked can refer to an appropriate connection between a EBV lmp promoter or regulatory element and a heterologous coding sequence (i.e., a non-lmp coding sequence, for example, a reporter gene) in such a way as to permit expression of the heterologous coding sequence.

Constructs suitable for use in the methods of the invention typically include, in addition to EBV lmp nucleic acid molecules, sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing EBV lmp nucleic acid molecules can be propagated in a host cell. As used herein, the term host cell is meant to include prokaryotes and eukaryotes. Prokaryotic hosts may include *E. coli, Salmonella typhimurium, Serratia marcescens* and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the present invention include oligonucleotide primers capable of acting as a point of initiation of nucleic acid synthesis within EBV lmp sequences. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the EBV template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min.

If the double-stranded nucleic acid is denatured by heat, the reaction mixture is allowed to cool to a temperature that promotes annealing of each primer to its target sequence on the EBV nucleic acid. The temperature for annealing is usually from about 35° C. to about 65° C. Annealing times can be from about 10 secs to about 1 min. The reaction mixture is then adjusted to a temperature at which the activity of the polymerase is promoted or optimized, i.e., a temperature sufficient for extension to occur from the annealed primer such that products complementary to the template nucleic acid are generated. The temperature should be sufficient to synthesize an extension product from each primer that is annealed to a nucleic acid template, but should not be so high as to denature an extension product from its complementary template (e.g., the temperature for extension generally ranges from about 40° to 80° C.). Extension times can be from about 10 secs to about 5 mins.

PCR assays can employ EBV nucleic acid such as DNA or RNA, including messenger RNA (mRNA). The template nucleic acid need not be purified; it may be a minor fraction of a complex mixture, such as EBV nucleic acid contained in human cells. DNA or RNA may be extracted from a biological sample such as dermal swabs, lymphoid tissue, cerebrospinal fluid, blood, sputum, bronchio-alveolar lavage, bronchial aspirates, lung tissue, and urine by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, extension reactions generally include 50 mM KCl, 10 mM Tris-HCl (pH 8.3), 1.5 mM $MgCl_2$, 0.001% (w/v) gelatin, 0.5-1.0 μg denatured template DNA, 50 pmoles of each oligonucleotide primer, 2.5 U of Taq polymerase, and 10% DMSO). The reactions usually contain 150 to 320 μM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target EBV nucleic acid molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996, 143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. Two oligonucleotide probes, each containing a fluorescent moiety, can hybridize to an amplification product at particular positions determined by the complementarity of the oligonucleotide probes to the target nucleic acid sequence. Upon hybridization of the oligonucleotide probes to the amplification product at the appropriate positions, a FRET signal is generated. Hybridization temperatures can range from about 35° C. to about 65° C. for about 10 secs to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer.

Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC™-Red 640, LC™-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as an LC™-Red 640-NHS-ester can be combined with C6-Phosphoramidites (available from ABI (Foster City, Calif.) or Glen Research (Sterling, Va.)) to produce, for example, LC™-Red 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPG's that require coupling of a fluorescein-NHS-ester after oligonucleotide synthesis.

Detection of EBV

Serological assays for EBV have been used to clinically detect EBV (see, for example, Klein, 1976, *Bull. Cancer*, 63:399-410). In recent years, PCR detection of EBV in patients diagnosed with lymphomas of the CNS has replaced cell culture techniques that have been ineffective for detecting herpesvirus species from CSF.

Several amplification assays have been reported for the qualitative and quantitative detection of EBV. These PCR assays require the use of conventional methods such as gel electrophoresis and Southern blotting for detection of amplified EBV DNA. These methods are labor intensive and frequently require more than one day to complete. Additionally, the manipulation of amplification products for the purpose of detection (e.g., by blotting) increases the risk of carry-over contamination and false positives. Further disadvantages of current PCR methods for detecting EBV include poor standardization of reagents and product amplification conditions, and the lack of general availability for use in all diagnostic and clinical laboratories.

The invention provides a qualitative and quantitative assay for detecting EBV. Identical PCR cycling conditions are used for both the qualitative and quantitative assays. The quantitative levels of EBV DNA are determined by processing individual samples containing known amounts of target EBV nucleic acid as standards along with samples from patients. The LightCycler PCR assay is the first automated, real-time system for the qualitative and quantitative detection of EBV DNA. The system is rapid (2-3 hours total sample preparation and analytical time), is sensitive (detects $\geq 10$ copies of EBV DNA/sample), specific (detects EBV DNA target exclusively), and has a wide dynamic linear range of $10^1$ to $10^7$ copies of EBV DNA/sample. By using commercially available real-time PCR instrumentation (e.g. LightCycler™, Roche Molecular Biochemicals, Indianapolis, Ind.), PCR amplification and detection of the amplification product can be combined in a single closed cuvette with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

The present invention provides methods for detecting the presence or absence of EBV in a biological sample from an individual. Methods provided by the invention avoid problems of sample contamination, false negatives, and false positives. The methods include performing at least one cycling step that includes amplifying an EBV portion of a lmp nucleic acid molecule from a sample using a pair of lmp primers, respectively. Each of the lmp primers anneals to a target within or adjacent to an EBV lmp nucleic acid molecule such that at least a portion of each amplification product contains nucleic acid sequence corresponding to lmp. More importantly, the amplification product should contain the nucleic acid sequences that are complementary to the lmp probes. The lmp amplification product is produced provided that EBV nucleic acid is present. Each cycling step further includes contacting the sample with a pair of lmp probes. According to the invention, one member of each pair of the lmp probes is labeled with a donor fluorescent moiety and the other is labeled with a corresponding acceptor fluorescent moiety. The presence or absence of FRET between the donor fluorescent moiety of the first lmp probe and the corresponding acceptor fluorescent moiety of the second lmp probe is detected upon hybridization of the lmp probes to the lmp amplification product.

Each cycling step includes an amplification step and a hybridization step, and each cycling step is usually followed by a FRET detecting step. Multiple cycling steps are performed, preferably in a thermocycler. Methods of the invention can be performed using the lmp primer and probe sets to detect the presence of EBV.

As used herein, "amplifying" refers to the process of synthesizing nucleic acid molecules that are complementary to one or both strands of a template nucleic acid molecule (e.g., EBV lmp nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

If amplification of EBV nucleic acid occurs and an amplification product is produced, the step of hybridizing results in a detectable signal based upon FRET between the members of the pair of probes. As used herein, "hybridizing" refers to the annealing of probes to an amplification product. Hybridization conditions typically include a temperature that is below the melting temperature of the probes but that avoids non-specific hybridization of the probes.

Generally, the presence of FRET indicates the presence of EBV in the sample, and the absence of FRET indicates the absence of EBV in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within 45 cycling steps is indicative of an EBV infection.

Methods of the invention also can be used for EBV vaccine efficacy studies or epidemiology studies. For example, an attenuated EBV in a vaccine can be detected using the methods of the invention during the time when the virus is still present in an individual. For such vaccine efficacy studies, the methods of the invention can be used to determine, for example, the persistence of an attenuated strain of EBV used in a vaccine, or can be performed in conjunction with an additional assay such as a serologic assay to monitor an individual's immune response to such a vaccine. In addition, methods of the invention can be used to distinguish one EBV strain from another for epidemiology studies of, for example, the origin or severity of an outbreak of EBV.

Representative biological samples that can be used in practicing the methods of the invention include dermal swabs, lymphoid tissue, cerebrospinal fluid, blood, sputum, bronchio-alveolar lavage, bronchial aspirates, lung tissue, and urine. Collection and storage methods of biological samples are known to those of skill in the art. Biological samples can be processed (e.g., by nucleic acid extraction methods and/or kits known in the art) to release EBV nucleic acid or in some cases, the biological sample can be contacted directly with the PCR reaction components and the appropriate oligonucleotides.

Melting curve analysis is an additional step that can be included in a cycling profile. Melting curve analysis is based on the fact that a nucleic acid sequence melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which the FRET signal is lost, the melting temperature of probes can be determined. Similarly, by detecting the temperature at which signal is generated, the annealing temperature of probes can be determined. The melting temperature(s) of the lmp probes from the respective amplification product can confirm the presence or absence of EBV in the sample.

Within each thermocycler run, control samples are cycled as well. Positive control samples can amplify EBV nucleic acid control template (e.g., a nucleic acid other than lmp) using, for example, control primers and control probes. Positive control samples can also amplify, for example, a plasmid construct containing an EBV lmp nucleic acid molecule. Such a plasmid control can be amplified internally (e.g., within the sample) or in a separate sample run side-by-side with the patients' samples. Each thermocycler run should also include a negative control that, for example, lacks EBV template DNA. Such controls are indicators of the success or failure of the amplification, hybridization and/or FRET reaction. Therefore, control reactions can readily determine, for example, the ability of primers to anneal with sequence-specificity and to initiate elongation, as well as the ability of probes to hybridize with sequence-specificity and for FRET to occur.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are necessary for accuracy in a diagnostic laboratory handling clinical samples.

Conventional PCR methods in conjunction with FRET technology can be used to practice the methods of the invention. In one embodiment, a LightCycler™ instrument is used. A detailed description of the LightCycler™ System and real-time and on-line monitoring of PCR can be found at biochem.roche.com/lightcycler on the World Wide Web The following patent applications describe real-time PCR as used in the LightCycler™ technology: WO 97/46707, WO 97/46714 and WO 97/46712. The LightCycler™ instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LightCycler™ thermal chamber. Addition of selected fluorescent dyes to the reaction components allows the PCR to be monitored in real time and on-line. Furthermore, the cuvettes serve as an optical element for signal collection (similar to glass fiber optics), concentrating the signal at the tip of the cuvette. The effect is efficient illumination and fluorescent monitoring of microvolume samples.

The LightCycler™ carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorometer, as part of the LightCycler™ apparatus, houses the light source. The emitted light is filtered and focused by an epi-illumination lens onto the top of the cuvette. Fluorescent light emitted from the sample is then focused by the same lens, passed through a dichroic mirror, filtered appropriately, and focused onto data-collecting photohybrids. The optical unit currently available in the LightCycler™ instrument (Roche Molecular Biochemicals, Catalog No. 2 011 468) includes three band-pass filters (530 nm, 640 nm, and 710 nm), providing three-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LightCycler™ can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBRGreenI® or SYBRGold® (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

As described herein, amplification products also can be detected using labeled hybridization probes that take advantage of FRET technology. A common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler™ Instrument. During FRET, the fluorescein transfers its energy to an acceptor fluorescent moiety such as LightCycler®-Red 640 (LC™-Red 640) or LightCycler™-Red 705 (LC™-Red 705). The acceptor fluorescent moiety then emits light of a longer wavelength, which is detected by the optical detection system of the LightCycler™ instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of EBV genomes).

Another FRET format utilizes TaqMan® technology to detect the presence or absence of an amplification product, and hence, the presence or absence of EBV. TaqMan® technology utilizes one single-stranded hybridization probe labeled with two fluorescent moieties. When a first fluorescent moietyis excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, CA) uses TaqMan® technology, and is suitable for performing the methods described herein for detecting EBV. Information on PCR amplification and detection using an ABI PRISM® 770 system can be found at appliedbiosystems.com/products on the World Wide Web.

Molecular beacons in conjunction with FRET also can be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

It is understood that the present invention is not limited by the configuration of one or more commercially available instruments.

Articles of Manufacture

The invention further provides for articles of manufacture to detect EBV. An article of manufacture according to the present invention can include primers and probes used to detect EBV, together with suitable packaging materials. Representative primers and probes for detection of EBV are capable of hybridizing to EBV lmp nucleic acid molecules. Methods of designing primers and probes are disclosed herein, and representative examples of primers and probes that amplify and hybridize to EBV lmp nucleic acid molecules are provided.

Articles of manufacture of the invention also can include one or more fluorescent moieties for labeling the probes or, alternatively, the probes supplied with the kit can be labeled. For example, an article of manufacture may include a donor fluorescent moiety for labeling one of the lmp probes and an acceptor fluorescent moiety for labeling the other lmp probe. Examples of suitable FRET donor fluorescent moieties and corresponding acceptor fluorescent moieties are provided above.

Articles of manufacture of the invention also can contain a package insert or package label having instructions thereon for using the lmp primers and probes to detect EBV in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims.

EXAMPLES

Example 1

Oligonucleotide Primers and Probes

Primers and probes were designed using the OLIGO software (Molecular Biology Insights, Inc., Cascade, OR). Primers were synthesized on a 0.2 µM scale by the Mayo Molecular Biology Core Facility (Rochester, MN). Probes were obtained from Idaho Technologies (idahotech.com/itbiochem/index on the World Wide Web). Sequences for primers and probes are shown in Table 1. The GenBank Accession numbers for the reference sequences used to design the primers and probes for each target are shown in Table 1, along with the relative location of each primer and probe.

TABLE 1

Primers and Probes for the Detection of EBV

| Gene Target | Gene Bank Accession # | Position (Product Size, bp) | Primer/ Probe Name | Sequence |
| --- | --- | --- | --- | --- |
| Latent membrane protein (lmp) | X81759 | 238 | lmp-F | 5'-ATG AGG AAC GTG AAT CTA ATG A-3' (Forward Primer) (SEQ ID NO:1) |
| | | | lmp-R | 5'-TAC AGA TAG ATG GCA CTC TTA CC-3' (Reverse Primer) (SEQ ID NO:2) |
| | | | lmp-FL | 5'-CTA CTC TCC ACG GGA TGA CTC ATC TCA ACA CA-3' (SEQ ID NO:3) |
| | | | lmp-RD | 5'-GAA GAA GCG GGC AGA GG-3' (SEQ ID NO:4) |

Primers were adjusted to 50 µM by measuring the $A_{260}$ of a 1/50 dilution (196 µl water+4 µl, Dilution Factor (DF) =50). The concentration was estimated by the following formula:

(µM found/50)×µl remaining)–µl remaining=water to add

Probes were dissolved in TE' to a concentration of 20 µM (supplied with the probes and resuspended according to manufacturer's instructions). The concentration of oligonucleotides and dye was double checked by UV absorption using the following equations from *Biochemica*, 1999,1:5-8:

$$[dye] = \frac{A_{dye}}{E_{dye}} \qquad [oligo] = \frac{A_{260} - \left(A_{260} \times \frac{E_{260(dye)}}{E_{dye}}\right)}{\frac{10^6}{nmol/A_{260}}}$$

| | Absorbance | | | |
|---|---|---|---|---|
| Dye | Abs max (nm) | $E_{dye}$ ($M^{-1}cm^{-1}$) | $E_{260(dye)}$ ($M^{-1}cm^{-1}$) | Emission Max (nm) |
| Fluorescein | 494 | 68,000 | 2,000 | 524 |
| LC Red 640 | 622 | 110,000 | 31,000 | 638 |

Plasmid controls were produced by cloning the lmp product amplified by the lmp primers into the 2.1 TOPO TA cloning vector (Invitrogen Corp., Carlsbad, Calif.). The recombinant vectors were transformed into chemically competent *E. coli* cells. The correct recombinant plasmid was confirmed and purified with a Wizard MiniPrep (Promega Corp., Madison, Wis.) Cleaning kit. The stock concentrations of the controls (in genomic equivalents) were determined. The plasmid containing the lmp insert was used to determine the analytical sensitivity of the assay. Plasmid concentration or the copy number of the gene target insert was determined with the following formula:
DS DNA, $A_{260}$ to molecules/µl
Given:
1. ($A_{260}$×Dilution Factor)/20=mg/ml=µg/µl DS DNA
   1 $A_{260}$=50 µg/ml
   1 $A_{260}$ (50)=µg/ml
   1 $A_{260}$ (50)/1000=µg/µl
2. ($6.02 \times 10^{23}$ molecules/mole)/($10^{12}$ pmole/mole) =$6.02 \times 10^{11}$ molecules/pmole
3. Base pairs of DNA in molecule=N
Then:
($A_{260}$×DF)/20 µg/µl×$10^6$ pg/µg×1 pmol/660 pg×1/N× $6.02 \times 10^{11}$ molecules/pmole=molecules/µl
Shortcut calculation:
(($A_{260}$×DF)/20)×($9.12 \times 10^{14}$/N)=molecules/µl

Example 2

PCR Conditions

Nucleic acids are extracted from 0.2 ml of cerebrospinal fluid (qualitative) or 1.0 ml anticoagulated (EDTA) blood (quantitative) from patients using the MagNA Pure instrument (Roche Diagnostics, Indianapolis, Ind.).

For the assay, a 5 µl aliquot of extracted nucleic acid was added to 15 µl of PCR reaction mixture in each reaction capillary. A no-target control received 15 µl of reaction mixture with 5 µl water.

| LightCycler ™TM Master Mix - EBV lmp | | | |
|---|---|---|---|
| Ingredient | Stock | Final | µl |
| Water | — | — | 4383.2 |
| Uracil-N-glycosylase | 10% | 0.2% | 192 |
| $MgCl_2$ | 50 mM | 4 mM | 768 |
| 10 X buffer | 10 X | 1 X | 960 |
| Primer-F | 50 mM | 0.7 µM | 134.5 |
| Primer-R | 50 mM | 0.7 µM | 134.5 |
| Platinum ® Taq | 5 U/ml | 0.03 U/ml | 57.6 |
| dNTP Plus | 10 mM | 0.2 µM | 192 |
| BSA | 2% | 0.025% | 120 |
| Probe-FL | 21 µM | 0.2 µM | 91.43 |
| Probe-RD | 23 µM | 0.4 µM | 166.96 |
| Total volume | | | 7200 |

The PCR reagents and specimen extract are centrifuged in the capillary to facilitate mixing. All capillaries are then sealed and amplified using the following protocol.

| Fluorescence Settings: | |
|---|---|
| LED Power | CALIB |
| F1 Gain | 1 |
| F2 Gain | 10 |
| Quantification Settings: | |
| Channel Settings | F2/F1 |
| Name of Program | |

Experimental Protocol:
Uracil-DNA glycosylase (1 cycle) Type: none
   37° C., 300 sec, 20°/sec slope
   95° C., 180 sec, 20°/sec slope
PCR (45 cycles) Type: Quantification
   95° C., 10 sec hold, 20° C./sec slope
   55° C., 15 sec hold, 20° C./sec slope, single acquisition
   72° C., 15 sec hold, 20° C./sec slope
Melt (1 cycle) Type: Melting Curve
   95° C., 0 sec hold, 20° C./sec slope
   45° C., 1 min hold, 20° C./sec slope
   85° C., 0 sec hold, 0.2° C./sec slope, continuous acquisition
Cool (1 cycle) Type: None
   40°, 30 sec hold, 20° C./sec slope The lmp primers and probes were used for both qualitative and quantitative EBV detection. Amplification of the EBV lmp sequences using the lmp primers disclosed herein results in a 238 bp amplification product.

Example 3

Quantitative Analysis of EBV

For quantitative analysis, ten-fold serial dilutions of the target gene plasmid were prepared to yield standardized levels of EBV lmp DNA ranging from $10^1$ up to $1 \times 10^{10}$. The serial dilutions were processed in the LightCycler instrument along with DNA extracted from a patient's EDTA-anticoagulated specimen. A curve plotting the cycle number (crossover point) versus the log of the concentration of DNA in each serial dilution was produced. The quantitative level of EBV DNA in patient sample was determined by comparison of the crossover point from the three standard dilutions of the target.

Example 4

Melting Curves

Following the completion of the amplification reaction, a melting curve analysis was performed by raising the temperature in the LightCycler™ thermal chamber from 50° C. to 85° C. at 0.2° C. per second. Fluorescent measurements were taken continuously as the temperature was raised and a melting curve was generated. The pair of lmp probes had a specific and characteristic melting curve from the lmp amplification product. The melting temperature (Tm) for the lmp product generated was about 62° C.

Example 5

Analytical Sensitivity

Serial dilutions of the EBV plasmid controls described in Example 3 were used to examine the sensitivity of the EBV LightCycler™ assay. The analytical sensitivity of the EBV LightCycler™ assay was at least 10 copies of the target sequence.

Example 6

Analytical Specificity

The following members of the Herpesvirus family were used to examine the specificity of the EBV LightCycler™ assay: HSV-1, HSV-2, VZV, CMV, HHV-6, HHV-7, HHV-8. In addition, nucleic acid from *S. aureus, S. epidermidis, E. coli*, and human cells was isolated and used to examine the specificity of the EBV LightCycler assay. The lmp primers and probes under the amplification conditions described herein did not cross-react with nucleic acid from any of the above-listed organisms.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An article of manufacture, comprising:
a pair of EBV latent membrane protein (lmp) primers, wherein said pair of EBV lmp primers comprises a first lmp primer and a second lmp primer, wherein said first lmp primer consists of the sequence 5'-ATG AGG AAC GTG AAT CTA ATG A-3' (SEQ ID NO:1) and wherein said second lmp primer consists of the sequence 5'-TAC AGA TAG ATG GCA CTC TTA CC-3' (SEQ ID NO:2);
a pair of EBV lmp probes, wherein said pair of EBV lmp probes comprises a first lmp probe and a second lmp probe, wherein said first lmp probe consists of the sequence 5'-CTA CTC TCC ACG GGA TGA CTC ATC TCA ACA CA-3' (SEQ ID NO:3) and wherein said second lmp probe consists of the sequence 5'-GAA GAA GCG GGC AGA GG-3' (SEQ ID NO:4); and
a donor fluorescent moiety and a corresponding acceptor fluorescent moiety.

2. The article of manufacture of claim 1, wherein said first lmp probe is labeled with said donor fluorescent moiety and wherein said second lmp probe is labeled with said corresponding acceptor fluorescent moiety.

3. The article of manufacture of claim 1, further comprising a package insert having instructions thereon for using said pair of lmp primers and said pair of lmp probes to detect the presence or absence of EBV.

* * * * *

UNITED STATES PATENT AND TRADEMARK OFFICE
CERTIFICATE OF CORRECTION

| | |
|---|---|
| PATENT NO. | : 7,365,176 B2 |
| APPLICATION NO. | : 10/255217 |
| DATED | : April 29, 2008 |
| INVENTOR(S) | : Thomas F. Smith and Mark J. Espy |

Page 1 of 1

It is certified that error appears in the above-identified patent and that said Letters Patent is hereby corrected as shown below:

Title Page, References Cited, Other Publications, col. 2, line 24, second Espy et al. reference, please delete "PCT" and insert --PCR-- therefor.

Signed and Sealed this

Twenty-sixth Day of August, 2008

JON W. DUDAS
*Director of the United States Patent and Trademark Office*